United States Patent [19]

Petrovic et al.

[11] 4,374,354
[45] Feb. 15, 1983

[54] RECHARGEABLE ELECTRIC PORTABLE APPLIANCE

[75] Inventors: John E. Petrovic; John Trenary, both of Ft. Collins, Colo.

[73] Assignee: Teledyne Industries, Inc., Ft. Collins, Colo.

[21] Appl. No.: 276,507

[22] Filed: Jun. 23, 1981

[51] Int. Cl.³ ............................................... H02J 7/00
[52] U.S. Cl. .................................... 320/2; 336/DIG. 2
[58] Field of Search ....................... 320/2; 336/DIG. 2

[56] References Cited

U.S. PATENT DOCUMENTS

| | | | |
|---|---|---|---|
| 3,277,358 | 10/1966 | Nicholl | 320/2 X |
| 3,418,552 | 12/1968 | Holmes | 320/2 |
| 3,463,994 | 8/1969 | Spohr | 320/2 |
| 3,633,089 | 1/1972 | Dorion, Jr. et al. | 336/DIG. 2 |
| 3,840,795 | 10/1974 | Rosyk et al. | 320/2 |

Primary Examiner—William M. Shoop
Attorney, Agent, or Firm—Hugh H. Drake

[57] ABSTRACT

An electric toothbrush housing contains a motor, a battery and a secondary coil coupled to charge the battery. An elongated magnetic core is disposed within that secondary coil. A well is defined in a base which receives a portion of the housing within which the secondary coil is positioned. In that base is a primary coil for inducing magnetic energy into the secondary coil. Disposed within the primary coil is an elongated stud of magnetic material. It is aligned axially with the core, so that respective end portions are mutually adjacent. One of those end portions is generally cup shaped and the other is formed and relatively oriented to nest within the first.

12 Claims, 16 Drawing Figures

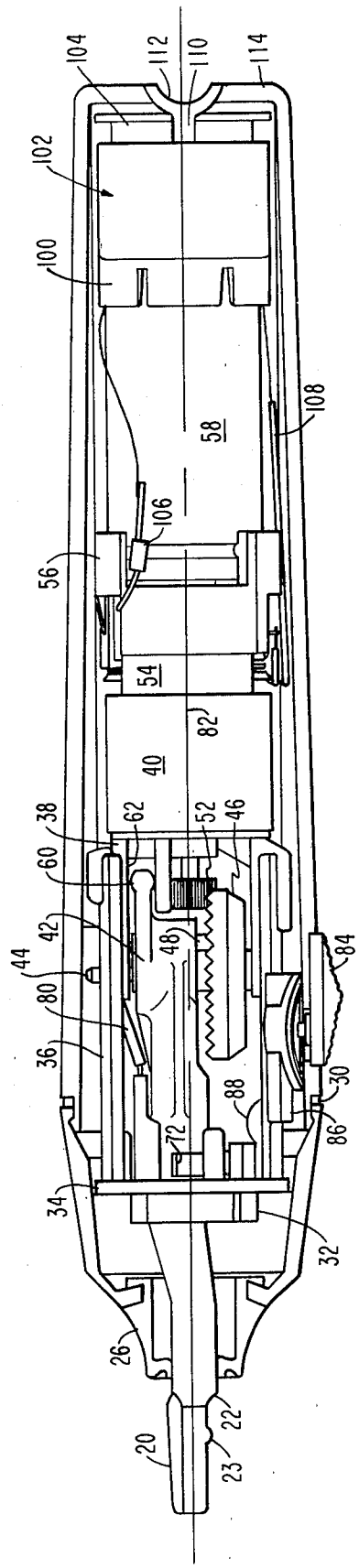
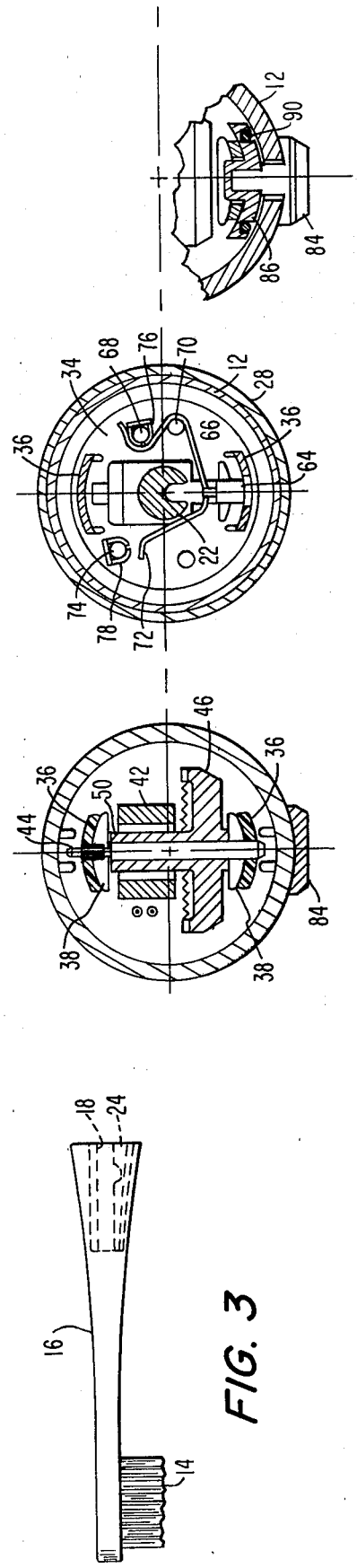
FIG. 2
FIG. 3
FIG. 4
FIG. 5
FIG. 6

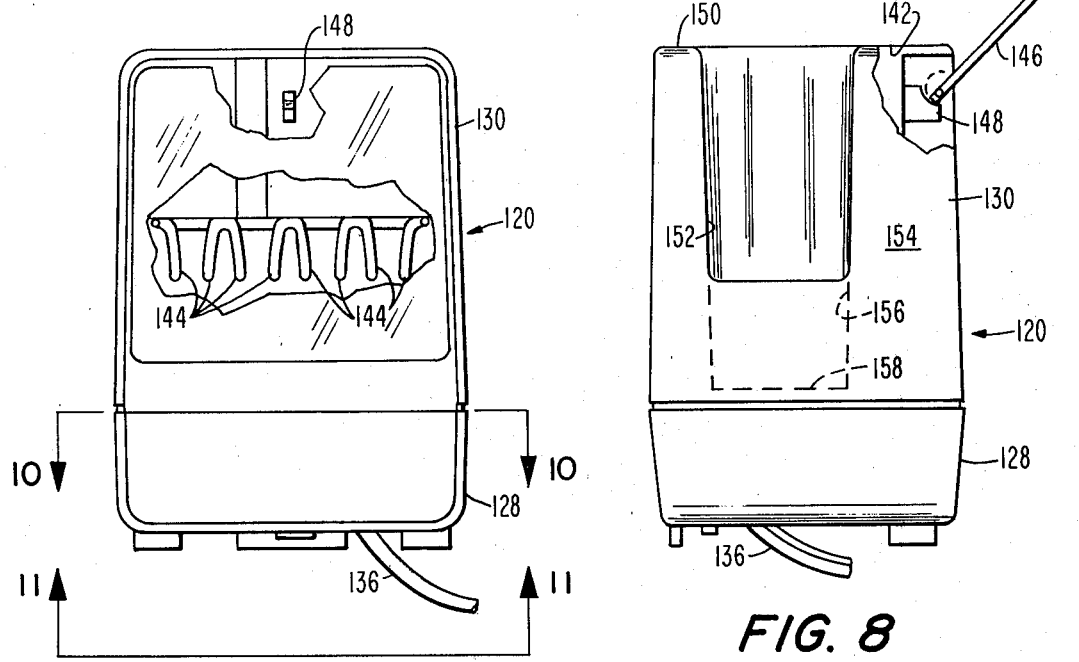
FIG. 7
FIG. 8
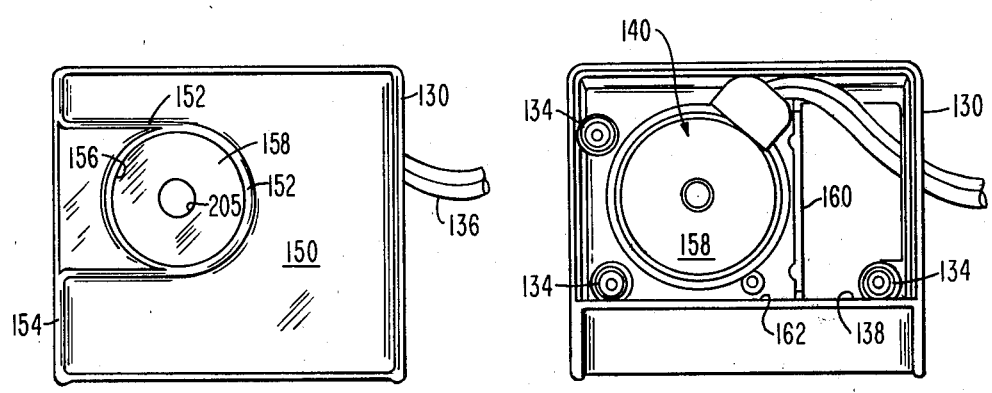
FIG. 9
FIG. 10
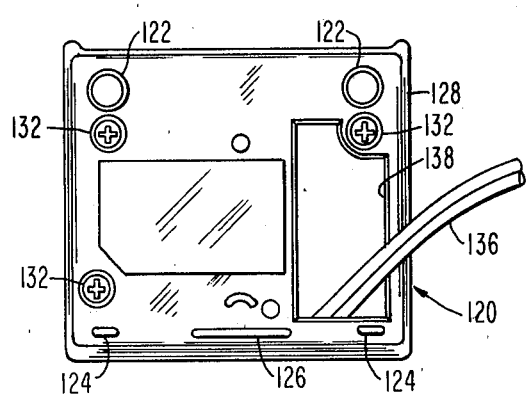
FIG. 11

RECHARGEABLE ELECTRIC PORTABLE APPLIANCE

The present invention pertains to a rechargeable electric portable appliance such as a toothbrush. More particularly, it relates to such an appliance which is insertable within a base unit for recharging of a self-contained battery.

Hand-held portable appliances, that use internally-contained rechargeable batteries, have become exceedingly popular and useful. In many cases, they also afford increased safety for the user. One example of both convenience and increased safety resides in the hand-held motor-driven electric toothbrush. Upon removing the power handle from the charging base unit, the toothbrush itself is entirely free if any connection to any level of electric power that otherwise could prove to be dangerous to the user in case of malfunction.

A typical example of such a portable electric toothbrush is that embodied in U.S. Pat. No. 3,510,747—Petrides. Related to that construction is the disclosure in U.S. Pat. No. 3,418,552—Holmes. In those approaches, a primary coil housed in a base unit has an elongated post of magnetic material that projects an extended distance within the base of the toothbrush housing during recharging. That post magnetically couples the primary coil in the base with a secondary coil in the bottom portion of the housing. Other magnetic-coupling arrangements have, of course, been known. Examples are U.S. Pat. Nos. 2,415,688—Hall, 2,967,267—Steinman et al. and 3,277,358—Nicholl.

In such prior art apparatus, there usually is a compromise as between the attainment of maximum efficiency of coupling within the magnetic assembly and convenience to or safety of the user. In electric toothbrushes, for example, the environment of use involves water which needs to be sealed against and the exposure of mating parts which may be contaminated and rendered less effective by reason of the build-up of the spillage of toothpaste or the accumulation of other matter. In the Petrides patent, for example, the upstanding post is exposed when the appliance is removed for use. That post is located in the way of convenient cleaning of the well that surrounds the upper end of the post and accepts the lower end of the power handle.

It is, accordingly, a general object of the present invention to provide a new and improved appliance which overcomes, minimizes or at least affords alternatives to problems and deficiencies such as those discussed above.

Another object of the present invention is to provide a new and improved rechargeable appliance that at least simplifies sealing problems and facilitates cleaning.

A further object of the present invention is to provide a new and improved appliance which affords design alternatives in the attainment of the degree of magnetic efficiency desired.

In accordance with one form of the present invention, a motor-driven portable appliance includes a housing of that appliance which contains electrically powered apparatus, a battery for energizing the apparatus and a secondary coil of electrically-conductive winding that is coupled to translate magnetically-induced energy to the batter. Disposed within the secondary coil is an elongated core of magnetically-permeable material. A base defines a well for supporting the portion of the housing within which the secondary coil is positioned. Included in the base is a primary coil responsive to applied power for magnetically inducing energy into the secondary coil. An elongated stud of magnetically-permeable material is disposed within the primary coil and also is aligned axially with the core so that the stud has an end portion adjacent to an end portion of the core. One of those end portions is generally cup shaped and the other of the end portions is formed and relatively oriented to nest within the one end portion.

The features of the present invention which are believed to be patentable are set forth with particularity in the appended claims. The organizaion and manner of operation of the invention, together with further objects and advantates thereof, may best be understood by reference to the following description taken in connection with the accompanying drawings, in the several figures of which like reference numerals identify like elements, and in which:

FIG. 2 is a fragmentary longitudinal cross-sectional view thereof taken along the line 2—2 in FIG. 1;

FIG. 3 is a side-elevational view of a component shown in FIG. 1;

FIG. 4 is a cross-sectional view taken along the line 4—4 in FIG. 1;

FIG. 5 is a cross-sectional view taken along the line 5—5 in FIG. 1;

FIG. 6 is a fragmentary cross-sectional view taken along the line 6—6 in FIG. 1;

FIG. 7 is a front elevational view, partially broken away, of a base unit associated with the toothbrush of FIG. 1;

FIG. 8 is a side elevational view, partially broken away, of the unit of FIG. 7;

FIG. 9 is a top plan view of the unit of FIGS. 7 and 8;

FIG. 10 is a view taken along the line 10—10 in FIG. 7;

FIG. 11 is a view taken along the line 11—11 in FIG. 7;

Figure 1:
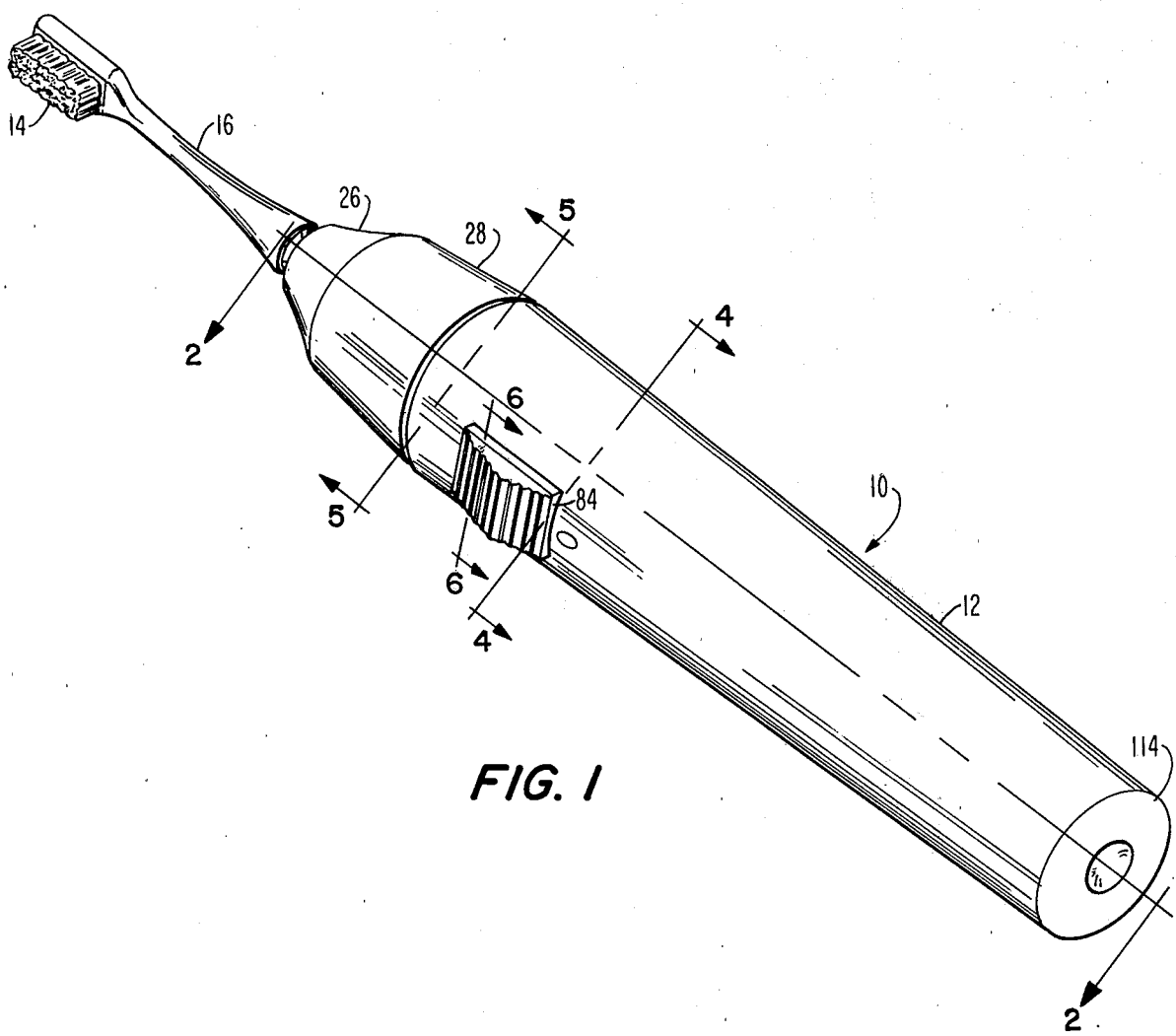
FIG. 1 is an isometric view of a portable motor-driven toothbrush.
Figure 12:
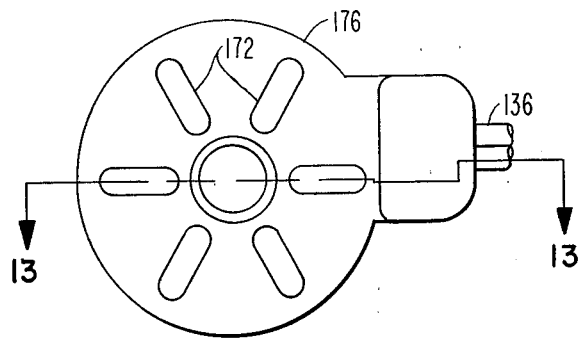
FIG. 12 is an end-elevational view of a component included within the apparatus of FIGS. 7-11.
Figure 13:
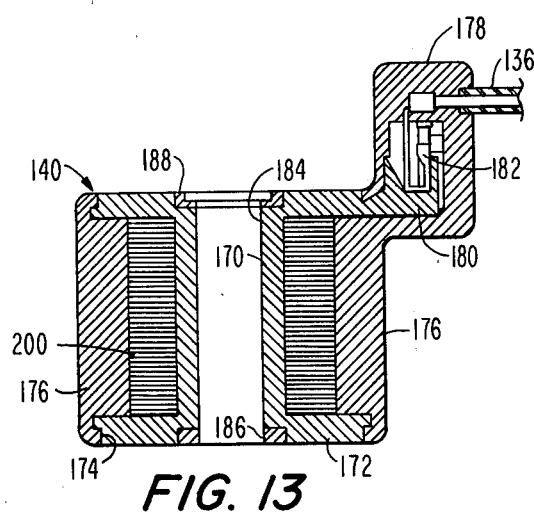
FIG. 13 is a cross-sectional view taken along the line 13—13 in FIG. 12.

In this case for purposes of illustration, the motor-driven portable appliance is in the form of a hand-held electric toothbrush 10. An elongated hollow housing 12 serves in use as the handle for the toothbrush. A brush head 14 projects laterally from the forward end portion of an elongated element 16 having an internal bore 18 (FIG. 3) of a shape which receives and mates with the end portion 20 of a shaft 22. The mating shapes of bore 18 and head 20 enable element 16 to be slipped into place upon head 20 in only one rotational position whereat element 16 is retained frictionally in place by cooperation of a nub 23 on head 20 and in integrally molded leaf spring 24 formed within bore 18.

Shaft 22 projects outwardly through a central opening in a flexible rubber boot 26 captivated in place by a generally-cylindrical cap 28 snap-fit around the outer periphery of the forward end of housing 12 in a manner to compress an O-ring or resilient seal 30.

Shaft 22 continues inwardly through a collar 32 which, as will be seen, constitutes a switch actuator and which is mounted to move laterally with respect to an adjacent disc 34 across the front of a bracket assembly 36. Bracket 36 is supoorted at its rear ends from a rigid framework 38 secured to the forward end of an electric motor 40, an apparatus requiring electric power.

Shaft 22 continues inwardly from disc 34 to a bearing 42 mounted around a pin 44 that also mounts a face gear 46. An axially offset stub 48 projects from gear 46 into the interior of bearing 42 which is of a generally oval shape. The combination of stub 48 and a sleeve 50 (FIG. 4) on pin 44 serves, upon rotation of gear 46, to cause bearing 42 to be eccentrically driven, so that shaft 22 is oscillated fore and aft. At the same time, the eccentric mounting causes the forward end of shaft 22 also to be oscillated back and forth in a lateral direction. The result is that brush head 14 is moved in an elliptical path.

A spur gear 52 turned by motor 40 drives face gear 46. Motor 40 includes a rearwardly-projecting brush assembly 54 to which is latched a mounting block 56 that receives, also by means of a snap-fit, one end of a rechargeable batter 48. Suitable leads, of course, connect the opposing poles of battery 58 to brush assembly 54 of motor 40.

Projecting on rearwardly from bearing 42 is a stabilizing arm 60 that is slidably received within a guideway 62 which is defined in the structure of framework 38. Projecting through disc 34 integrally from collar 32 is a switch operator 64 (FIG. 5). A conductive, resilient flat spring 66 is carried from disc 34 by means thereon of rearwardly projecting posts 68 and 70 upon which spring 65 is frictionally engaged. From post 70, spring 66 continues beneath operator 34 to a location wherein its free end 72 is normally spaced from another post 74 that projects rearwardly from disc 34 but which free end is movable upon actuation of operator 64 so as to be moved positively toward post 74. Affixed on posts 68 and 74 are respective contacts 76 and 78 from which corresponding wires, as at 80, lead to motor 40 and brush assembly 54 to permit actuation of the motor when spring 66 bridges contacts 76 and 78.

Any time that shaft 22 is moved laterally in a direction to force collar 32 toward a location centrally of the longitudinal axis 82 of housing 12, operator 64 presses upon spring 66 so that its free end 72 engages contact 78 and completes the electrical circuit that energizes the motor. Alternatively, a switch button 84 pin-coupled to a switch slide 86 may be user-actuated to cause a finger 88 (FIG. 2), on slide 86, to cam atop switch operator 64 and effect operation of the latter to move spring contact 66 into its closing relationship with contact 78. A resilient O-ring 90 completes a seal between slide 86 and the interior wall of housing 12.

Figure 14:
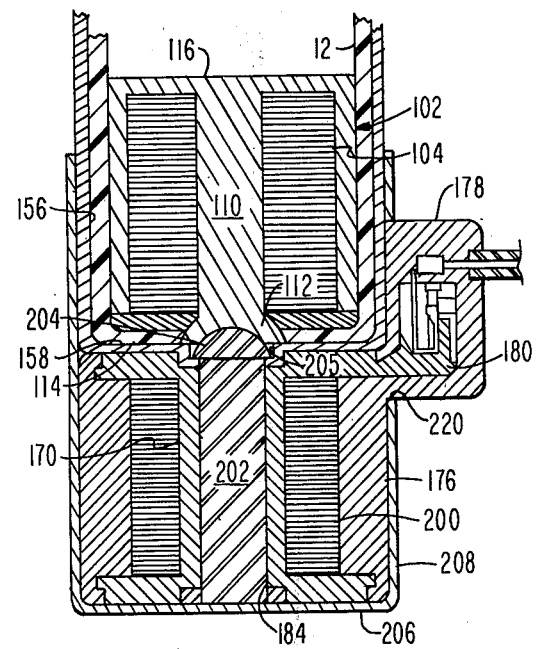
FIG. 14 is an enlarged, fragmentary cross-sectional view of a lower portion of the apparatus of FIGS. 1 and 2 as combined with the apparatus of FIGS. 7-13.

Frictionally carried upon the still-further inward end of battery 58 is a sleeve 100 that is snap fit to a secondary assembly 102 of a battery charger. In accordance with one embodiment is illustrated in FIG. 14, secondary assembly 102 includes a wound coil 104 of electrically-conductive wire. One end of coil 104 is connected through a diode 106 to one end of battery 58, while the other end of coil 104 is connected to the other end of battery 58 that also is connected, by means of a lead 108, into the motor and brush assembly.

Figure 16:
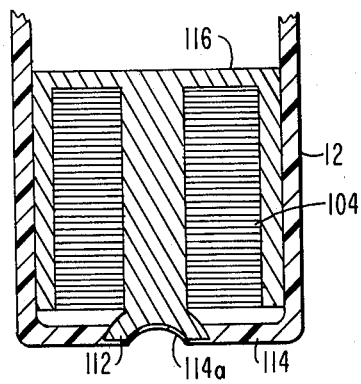
FIG. 16 is a fragmentary cross-sectional view showing an alternative for a portion of that which is shown in FIG. 14.

Disposed within coil 104 is an elongated core 110 of magnetically-permeable material. Core 110 is flared at its most rearward end to define a generally cup-shaped portion 112 located centrally within the bottom and closing end wall 114 of housing 12. As specifically shown, core portion 112 is exposed at the rear of housing 12 and wall 114 is sealed snugly therearound. In an alternative, end wall 114 continues, preferably thinly, over the rearwardmost surface of cup-shaped portion 112 (end wall 114a in FIG. 16). Physically connected at its closed end to core 110, or at least closely coupled in a magnetic sense thereto, is a metallic cup 116 that seats over the top or inward end of coil 104 and extends down around its outer side walls, so as best to complete a magnetic enclosure for coil 104.

Cooperating with toothbrush 10 is a base 120 (FIGS. 7-11) having feet 122, 124 and 126 projecting from its bottom so as to enable the base to sit on a countertop or the like. In this case, those feet project downwardly from a lower casing 128 atop which is mounted an upper casing 130 with those casings being secured together by means of screws 132 threaded into posts 134 that project downwardly within the interior of upper casing 130. The feet on the bottom of lower casing 128 are of a length sufficient to allow a power supply cord 136 to be led from the surface of the countertop or the like through an opening 138 to a power assembly 140 yet to be further described.

A recess 142 formed into one side of upper casing 130, and matchingly formed on the same side of lower casing 128, accommodates the storage of a plurality of toothbrush elements 16 by means of a laterally spaced plurality of clips 144. A door 146 is hinged by pins at its sides from he internal wall of recess 142 so as to enable it to be swung open. When open, the upper edge margin of door 146 cams against a lug 148 so that the door will hold in an open position. Preferably, door 146 is transparent, although shaded, so as to allow observation of the toothbrush elements as stored within the unit.

Formed into the top 150 of upper casing 130 is a generally U-shaped cavity 152 that opens also through one sidewall 154 of upper casing 130. Projecting downwardly from the bottom of cavity 154 is a well 156 shaped and sized to receive the lowe end portion of housing 12 that laterally embraces coil assembly 102 and includes wall 114, with wall 114 thereupon lying against the bottom 158 of well 156. Both for charging of battery 58 as well as simply for storage of electric toothbrush 10 when not in use, the toothbrush thereupon is seated within well 156.

An upwardly projecting wall 160 within lower casing 128 defines a compartment 162 within which primary coil assembly 140 is located. A coil 200 is wound around an electrically-insulative but magnetically-conductive bobbin 170 which carries lugs 172 that seat in openings 174 formed into an encapsulating sleeve and end wall assembly 176. At one side of each, extensions 178 and 180 of the bottom of the sleeve complete a connector assemblage 182 within which power cord 126 is connected to the respective two ends of coil 200. After the exposed ends of the power cord are joined to the leads from coil 200, the two different basic parts, the bottom and the sleeve, preferably are joined together by ultrasonic welding. As an alternative, the whole primary coil assembly could be potted in one operation.

Bobbin 170 defines an internal bore 184. In this case, the bore is preferably defined at opposing ends of bobbin 170 by circular inserts 186 and 188. However, the structural openings of those inserts may be defined by bobbin 170 directly.

Disposed in a space defined between bobbin 170 and sleeve 176 is primary coil 200 already mentioned. Located centrally within the interior of coil 200 is an elongated stud 202. At one end portion, stud 202 is shaped to define a head 204 of a size and shape to nest within end portion 112 of core 110.

Preferably, head 204 is disposed through but sealed within a central opening 205 in bottom wall 158 of well 152, so as to allow a maximum efficiency of magnetic coupling between head 204 and end portion 112 of core 110. Alternatively, however, bottom wall 158 may continue, preferably in as thin a form as feasible, over the outer end of head 204.

At its other end, stud 202 is magnetically coupled and preferably even mechanically affixed into the center of the bottom wall 206 of an upstanding and tall cup 208 formed of magnetic material. If desired for manufacturing efficiency, the sidewalls of cup 208 may be separately formed as a cylinder and joined to bottom wall 206 along and around an upturned periphery of the latter. In any case, the lower portion of the sidewall of cup 208 surround primary coil 200. That sidewall, however, preferably extends into an upper portion that surround and embraces well 156 so as also to embrace coil 104 when the lower end portion of housing 12 is inserted within the well.

The result of the foregoing assemblage is that, when the toothbrush unit is inserted within the well in the base, a rather highly efficient magnetic coupling is established between primary coil 200 and secondary coil 104. Of course, this is achieved in the instant embodiment by way of close coupling between stud 202, core 110, cap 116 and upstanding cup 208.

Figure 15:
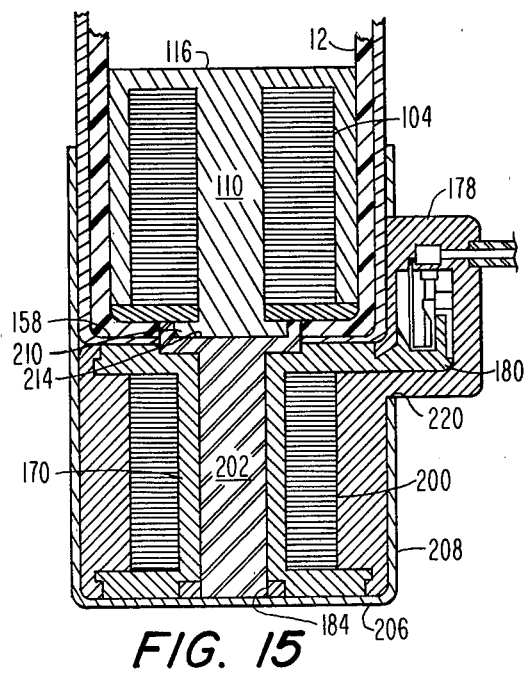
FIG. 15 is a view similar to FIG. 14 but depicting an alternative thereto.

In one modification contemplated, the solid-semi-hemispherical shape of head 204 is placed upon the lower end of core 110, and the cup-shaped semi-hemispherical segment 112 of lower end portion 110 is formed upon the upper end of stud 202 instead of upon the lower end of core 110. Another alternative is illustrated in FIG. 15. In this case, core 110 is formed at its lower end to define a disc 210 that seats snugly within an upwardly facing cup 214 (all of magnetic material, of course) that is affixed atop stud 202. Even then, the relative postions of disc 210 and cup 214, with respect to core 110 and stud 202, could be reversed.

It should be noted that, as illustrated, extensions 178 and 180 protrude through an opening 220 formed into the sidewall 208 of the lower magnetic cup. As a further alternative, however, the manner of coupling the power lead 136 into primary coil 200 could be arranged to enter from the bottom of the unit or through a more-limited opening in the sidewall.

In each case illustrated, the internal magnetic circuit, around the coils, is completed by a cup-shaped element that cooperates with another element nestable therein. A somewhat equivalent result may be obtained, in the alternative, by arranging both of the heads of the core and the stud to be in a cup-shaped form. In that case, it is contemplated that the cup-shaped element on the upper end of the stud within the primary winding would nest between the primary and secondary coils and the cup-shaped element affixed to the core within the secondary coil wouold nest just outside that secondary coil.

Numerous variations have been disclosed for attaining at least reasonably efficient operartion of a rechargeable-type of battery-operated appliance. While a specific embodiment has been illustrated in connection with a toothbrush, it is clear that other appliances, at least those of the hand-held variety, also may benefit from use of the present disclosure. In general, all approaches disclosed enable the assembly of a hand-held unit that cooperates with the base unit, for charging, while yet avoiding undue problems with cleaning, maintenance or other parameters of continued use. Yet, these problems are overcome without imparting to the approach an unreasonable degree of magnetic inefficiency in the design of the charging unit.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of that which is patentable.

We claim:

1. A portable appliance comprising:
    a housing of said appliance that contains electrically powered apparatus, a battery for energizing said apparatus and a secondary coil of electrically-conductive winding that is coupled to translate magnetically-induced energy to said battery;
    an elongated core of magnetically-permeable material disposed within said secondary coil;
    a base that defines a well for supporting the portion of said housing within which said secondary coil is positioned and which includes a primary coil of electrically-conductive winding that is responsive to applied power for magnetically inducing energy into said secondary coil;
    an elongated stud of magnetically-permeable material disposed within said primary coil, said stud being aligned axially with said core and having an end portion adjacent to an end portion of said core, one of said end portions being generally cup shaped and the other of said end portions being formed and relatively oriented to nest within said one end portion.

2. An appliance as defined in claim 1 in which said one end porion is a segment of a hollow sphere and in which said other end portion is a segment of a solid sphere of a size to nest snugly within said hollow sphere.

3. An appliance as defined in claim 1 in which said one end portion generally defines a bottom wall joined to a surrounding wall disposed laterally to said bottom wall and in which said other end portion defines a plate of a conformation to seat snugly within said surrounding wall.

4. An appliance as defined in claim 1 in which said one end portion is formed on said core and projects toward said stud.

5. An appliance as defined in claim 1 in which said one end portion is formed on said stud and projects toward said core.

6. An appliance as defined in claim 1 which further includes:
    an elongated cup of magnetically-permeable material from the bottom of which said stud projects within the surrounding wall of said elongated cup, said primary winding being nested with the bottom portion of said surrounding wall and around said stud, and said well being nested within the upper portion of said surrounding wall.

7. An appliance as defined in claim 1 in which at least a portion of the bottom wall of said housing, beneath said secondary coil, faces and is adjacent to at least a portion of the bottom wall of said well beneath which said primary coil is disposed.

8. An appliance as defined in claim 1 in which the end portion of said core extends through but is sealed within a bottom wall of said housing.

9. An appliance as defined in claim 1 in which a bottom wall of said housing overlies and is adjacent to the end portion of said core.

10. A portable appliance comprising:
a housing of said appliance that contains electrically powered apparatus, a batter for energizing said apparatus and a secondary coil of electrically-conductive winding that is coupled to translate magnetically-induced energy to said battery;
a base that defines a well for supporting the portion of said houing within which said secondary coil is positioned and which includes a primary coil of electrically-conductive winding that is responsive to applied power for magnetically inducing energy into said secondary coil;
magnetically-permeable material disposed within said primary and secondary coils for coupling magnetic flux therebetween;

said base further including means defining a U-shaped cavity aligned atop said well and open through a sidewall of said base.

11. An electric toothbrush unit comprising:
a housing for said toothbrush unit that contains a motor, a battery for energizing said motor and a secondary coil of electrically-conductive winding that is coupled to translate magnetically-induced energy to said battery;
a base that defines a well for supporting the portion of said housing within which said secondary coil is positioned and which includes a primary coil of electrically-conductive winding that is responsive to applied power for magnetically inducing energy into said secondary coil;
magnetically-permeable material disposed within said primary and secondary coils for coupling magnetic flux therebetween;
a plurality of brush elements selectively engageable with said unit;
means defining a recess in a side of said base;
means disposed within said recess for removeably securing said brush elements for storage;
and a manually-openable door covering said recess.

12. A unit as defined in claim 11 which further includes:
a hinge integrally formed within said recess;
a mating hinge element formed on said door;
and a lug integrally formed within said recess and against which a margin of said door is engaged to hold said door in an open position.

* * * * *